(12) United States Patent  
Berns et al.

(10) Patent No.: US 9,321,990 B2  
(45) Date of Patent: Apr. 26, 2016

(54) SYSTEMS AND METHODS FOR IDENTIFYING AND DISRUPTING CELLULAR ORGANELLES

(75) Inventors: Michael W. Berns, Irvine, CA (US); Thoru Pederson, Worchester, MA (US); Elliot Botvinick, Irvine, CA (US); Linda Zhixia Shi, Vista, CA (US)

(73) Assignees: The Regents of the University of California, Oakland, CA (US); University of Massachusetts, Boston, MA (US)

(*) Notice: Subject to any disclaimer, the term of this patent is extended or adjusted under 35 U.S.C. 154(b) by 925 days.

(21) Appl. No.: 13/234,986

(22) Filed: Sep. 16, 2011

(65) Prior Publication Data

US 2012/0129158 A1 May 24, 2012

Related U.S. Application Data

(63) Continuation of application No. 11/865,677, filed on Oct. 1, 2007, now abandoned.

(60) Provisional application No. 60/848,513, filed on Sep. 29, 2006.

(51) Int. Cl.
| | | |
|---|---|---|
| *C12Q 1/00* | (2006.01) |
| *H01S 3/00* | (2006.01) |
| *G01N 35/08* | (2006.01) |
| *C12M 1/42* | (2006.01) |
| *C12M 1/00* | (2006.01) |
| *G01N 15/14* | (2006.01) |

(52) U.S. Cl.
CPC .............. *C12M 35/02* (2013.01); *C12M 47/06* (2013.01); *G01N 15/1475* (2013.01); *G01N 2015/149* (2013.01); *Y10T 436/12* (2015.01)

(58) Field of Classification Search
None
See application file for complete search history.

(56) References Cited

U.S. PATENT DOCUMENTS

| | | | |
|---|---|---|---|
| 6,322,556 B1* | 11/2001 | Gwon et al. | 606/6 |
| 6,967,335 B1 | 11/2005 | Dyer et al. | |
| 7,045,772 B2* | 5/2006 | Moellmann et al. | 250/234 |
| 2002/0103478 A1* | 8/2002 | Gwon et al. | 606/4 |
| 2003/0107732 A1* | 6/2003 | Sasaki et al. | 356/318 |
| 2004/0238719 A1* | 12/2004 | Moellmann et al. | 250/203.1 |
| 2005/0046936 A1* | 3/2005 | Dixon et al. | 359/385 |
| 2006/0167344 A1* | 7/2006 | Mizumo | 600/168 |
| 2006/0261263 A1* | 11/2006 | Ishihara et al. | 250/234 |

OTHER PUBLICATIONS

Varvani-Farahani, A. et al "Short Crack Detection Using Confocal Scanning Laser Microscopy (CSLM) Technique" online <URL: http://www.ryerson.ca/~avarvani/CSLM.htm>, archived Feb. 13, 2005, accessed Mar. 22, 2014, 2 pages.*
Grier, D.G. "A Revolution in Optical Manipulation" Nature, Aug. 14, 2003, 424, pp. 810-816 (doi:10.1038/nature01935).*
UCSD "Optical Trap: The Single-Beam Gradient Force" UCSD Modern Physics Lab Guide, Oct. 1, 2002, 10 pages.*

(Continued)

*Primary Examiner* — Rosanne Kosson
*Assistant Examiner* — Aaron J Kosar
(74) *Attorney, Agent, or Firm* — Fish & Richardson P.C.

(57) ABSTRACT

This invention relates to optomechanical systems and methods for altering, modifying or disrupting a target object. Such systems and methods are used for, for example, ablating the endogenous nucleus in a cell.

20 Claims, 10 Drawing Sheets

(56) References Cited

OTHER PUBLICATIONS

Conia, J, et al "The Micro-Robotic Laboratory: Optical Trapping and Scissing for the Biologist" J. Clin. Lab. Anal., 1997, 11, pp. 28-38.*
Lehr, Hans-Anton; Mankoff, David A; Corwin, David; Santeusanio, Guiseppe; Gown, Allen M "Application of Photoshop-based Image Analysis to Quantification of Hormone Receptor Expression in Breast Cancer" Journal of Histochemistry & Cytochemistry, 1997, 45, pp. 1559-1565 (DOI: 10.1177/002215549704501112).*
Sheetz, Michael P. (ed) (1998) "Laser Tweezers in Cell Biology" Methods in Cell Biology, vol. 55, 228 pp. (ISBN: 978-0-12-564157-9) (Chapters. 2, 5, 7, 11, and 12 only).*
Ted's Photographics "Digital Image Processing" The Science of Photography, Feb. 2001, 8 pages.*
Botvinick, E. L. et al., "Internet-based robotic laser scissors and tweezers microscopy," *Microsc. Res. Tech.*, 68:65-74 (published online, Oct. 14, 2005).
Botvinick, E. L. et al., "Controlled Ablation of Microtubules Using a Picosecond Laser," *Biophysical Journal*, 87:4203-4212 (2004).
Wakida N. et al., "Laser nanosurgery of single microtubules reveals location-dependent depolymerization rates," *J Biomed Opt*, 12:024022-1-024022-8 (2007).
Gomez-Godinez V. et al., "Recruitment of DNA damage recognition and repair pathway proteins following near-IR femtosecond laser irradiation of cells," *J Biomed Opt*, 12:020505-1-020505-3 (2007).

* cited by examiner

SYSTEMS AND METHODS FOR IDENTIFYING AND DISRUPTING CELLULAR ORGANELLES

CROSS REFERENCE TO RELATED APPLICATIONS

This application claims priority under 35 U.S.C. §120 as a continuation of U.S. patent application Ser. No. 11/865,677, filed Oct. 1, 2007, which claims the benefit of priority under 35 U.S.C. §119 to U.S. provisional Application Ser. No. 60/848,513, filed Sep. 29, 2006, the disclosures of which are incorporated herein by reference.

STATEMENT REGARDING FEDERALLY SPONSORED RESEARCH

Procedures set forth in this application were supported in part by Grant No. NIH RR 14892 awarded by the National Institute of Health, and by Grant No. AFOSR No. F9620-00-1-0371 awarded by the United States Air Force. The government may have certain rights in any inventions derived therefrom.

TECHNICAL FIELD

Provided herein are systems and methods for the alteration, modification or disruption of target organelles and/or regions in a cell or group of cells.

BACKGROUND

Systems and methods for disrupting cellular organelles have been developed. Conventional systems generally rely on direct user interface to perform the necessary capture and ablation procedure on a targeted cell. Accordingly, conventional systems rely on the presence of a technician or other end-user in order to design, manipulate, sort, assemble, trap and disrupt a target object, such as a cellular organelle.

SUMMARY

The application relates, in general, to the field of systems and methods for altering, modifying or disrupting a target object or portion thereof. A target object includes a cell or selected region in a cell such as an organelle. The cell or portion thereof can be associated with a carrier, such as a bead or other carrier that facilitates movement and/or detection of the cell in an optomechanical system.

In particular, the present application relates to optomechanical systems that correlate image acquisition of a target object with the controlled application of electromagnetic radiation to the target. An optomechanical system provided herein can be used in association with fluidic transport elements that transport and position objects in an environment suitable for imaging and electromagnetic radiation application. Embodiments of a system include a remote controller for remotely controlling image acquisition and radiation application. In some embodiments, a system is adapted to identify a target object in the absence of operator intervention. In other embodiments, a target object is identified by an operator. According to various embodiments, a system can be remotely controlled via a graphical user interface. The user interface may be viewed from a host computer or from a remote site.

In one embodiment, an optomechanical system is provided. The system includes a platform configured to accommodate at least one target object or portion thereof in a fluid medium. A target object includes a cell, an organelle, a cell or organelle complexed with a carrier, or any combination thereof. A system further includes a detector assembly operationally associated with the platform and configured to capture images associated with a target object contained in the fluid medium; at least one radiation source coupled to the detector assembly and operationally configured to emit a pattern of radiation sufficient to specifically disrupt the target object; and a controller operationally associated with the detector assembly and the radiation source. In general, and in the specific embodiments claimed, the controller is configured to coordinate the pattern of radiation emission from the radiation source with the image of the target object captured by the detector assembly. In some aspects the platform is associated with a fluidic flow path. The flow path can be connected to a reservoir that includes a one or more target objects such as cells or portions thereof. In one aspect the fluid flow path is a microfluidic flow path.

In some aspects the object is a cell, such as an embryonic stem cell. In other aspects, the object is an organelle. In still other aspects, a portion of a target object, such as an organelle is targeted for disruption. The portion of a cell can be a nucleus. In other aspects the portion of a cell can be a mitochondrion, chloroplast or any other nucleic acid-containing cellular structure such as a ribosome, nucleolus, inter-chromatin granule cluster, cytoplasmic P-body or any site of replication by a DNA or RNA virus, viroid or other nucleic acid-containing entity.

In some embodiments, a controller associated with a system of the invention can be operated by a user. In some aspects, the user is a remote user.

In other aspects, the controller is configured to determine a profile of the target object based on the images of the target object. The controller can be further configured to synchronize entry of an object in to a flow path associated with a platform. The flow path may be connected to a reservoir. The platform may be associated with image detection by the detector assembly and radiation emission from the radiation source.

In some embodiments, the radiation source included in a system provided herein is a laser. The laser can be a gas laser, a solid-state laser, a tunable dye laser, or semiconductor laser.

In some aspects, the detector assembly includes a complementary metal oxide semiconductor (CMOS) imager, a charge coupled device (CCD) imager, a camera with photosensitive film, a fluorescence imager, a Vidicon camera, or any combination thereof.

In another embodiment, a method of disrupting an object is provided. The method includes directing an object, such as a cell, in to a flow path; imaging a target object or portion thereof; generating a profile of the object based upon the image; and exposing the target object to a radiation emission sufficient to specifically disrupt the target object. In general the pattern of radiation emission is determined by the profile of the object.

In another embodiment, a method for identifying and disrupting a target object is provided. The method includes directing an object in to a flow path; imaging a target object; outlining the image of the object; generating a profile of the object by digitizing the outlined image; transmitting the profile of the object to a controller; contacting the target object or portion thereof to radiation suitable for disrupting the target object or portion thereof, wherein the contacting includes: i) emitting radiation in a pattern determined by the profile of the object; ii) translocating the emitted radiation in a pattern determined by the profile of the object; or iii) maintaining the emitted radiation substantially stationary while translocating the object in a pattern determined by the profile of the object, thereby exposing the target object to a pattern of radiation emission sufficient to specifically disrupt the target object. In some embodiments trapping radiation is applied to the object in order to maintain the position of the object.

In another embodiment, an article of manufacture is provided. The article includes a computer usable medium having computer readable program code means embodied therein for causing an optomechanical system to image a target organelle associated with a cell; outline the image of the organelle; generate a profile of the organelle; transmit the profile of the organelle to a controller operationally associated with a movable reflective surface; and expose the target organelle to a pattern of radiation emission sufficient to specifically disrupt the target organelle.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

Like reference symbols in the various drawings indicate like elements.

DETAILED DESCRIPTION

The application provides optomechanical systems and methods for efficient inactivation of either a selected cellular organelle or a specific region of the cell.

Figure 1:
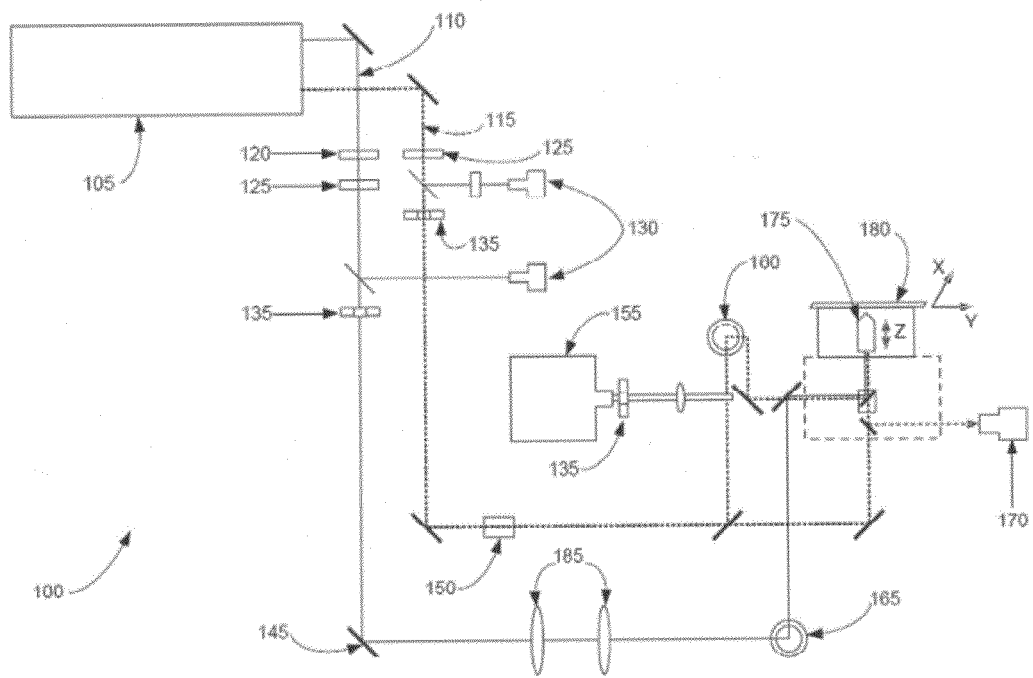
FIG. 1 depicts exemplary external laser radiation paths of a system.
Figure 2:
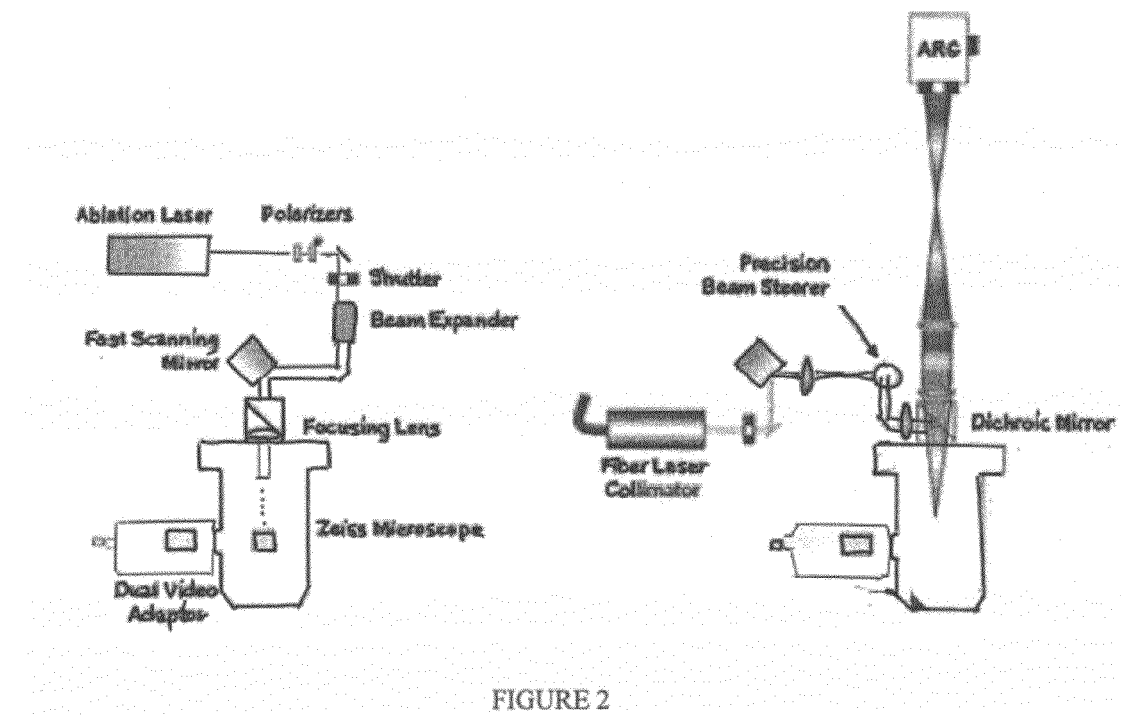
FIG. 2 depicts exemplary internal radiation paths of a system.

FIG. 1 depicts an exemplary embodiment of an optomechanical system. In the embodiment of FIG. 1, a single emitter 105 includes two laser lines designated trapping laser line 110 and ablation laser line 115. An exemplary emitter is an ND:YAG pulsed laser including a 75 MHz repetition rate. In other embodiments more than one emitter can be used to supply a trapping laser line, ablation laser line, or any other electromagenetic radiation line suitable for use with an optomechanical system. For example, FIG. 2 depicts an exemplary system that includes separate emitters for the trapping laser and the ablation laser. Accordingly, in the context of an optomechanical system it is understood that the term "emitter" includes single as well as multiple emitters that provide trapping, ablation and other electromagentic radiation to a system.

Referring again to FIG. 1, trapping laser 110 comprises a wavelength of between 750 nm and 1250 nm with between 50 femtosecond (fs) and 100 picosecond (ps) pulse durations. Ablation laser 115 comprises a wavelength that is substantially double that of trapping laser frequency (e.g., 375 nm to 625 nm) with between 50 fs and 100 ps pulse duration. With regard to pulse duration, it is understood that emitters capable of emitting laser pulses in the range of femto- to pico-second durations are suitable for use in an optomechanical system. Exemplary emitters are set forth in "Laser nanosurgery of single microtubules reveals location-dependent depolymerization rates" (Journal of Biomedical Optics, Vol. 12(2), 024022-1 to 024022-8, March/April 2007) and in "Recruitment of DNA damage recognition and repair pathway proteins following near-IR femtosecond laser irradiation of cells" (Journal of Biomedical Optics, Vol. 12(2), 020505-1 to 020505-3, March/April 2007), the contents of which are incorporated herein by reference in their entirety.

Referring again to FIG. 1, each laser line may be controlled independently via polarizer 125. In some aspects, polarizer 125 may be included in a motorized rotary mount. Power meters 130 may be operatively associated with ablation laser line 115 and trapping laser line 110. Ablation laser 115 and trapping laser 110 are sampled and measured by mechanical shutters 135 to select laser power before exposure. Beam expander 150 expands ablation laser line 115 and beam expander 185 expands trapping laser line to increase numerical aperture. In some aspects ablation laser line 115 and trapping laser line 110 are directed to the back aperture of the objective lens mounted in an inverted microscope. In some embodiments, beam splitters and shutters are used to combine ablation laser line 115 and trapping laser line 110 with radiation emitted from arc lamp 155 for simultaneous laser exposure and fluorescence excitation through the epifluorescence port or through bottom port 175. Tower 1 160 and tower 2 165 raise the laser lines to the height of the microscope. An optional dual view imaging system and a sensitive camera allow for low light level imaging, FRAP, FRET and ratio imaging techniques. A microfluidic flow path containing a target object or portion thereof and associated with platform 180 is exposed to ablation laser line 115 and trapping laser line 110, and optionally electromagnetic radiation from arc lamp 155. It is understood that a target object includes a cell, an organelle, a cell or organelle complexed with a carrier, or any combination thereof. While the terms "cell" and "organelle" are used in the examples provided below, it is understood that a target object includes any object suitable for detection and disruption by an optomechanical system provided herein.

Detector assembly 170 detects the image of an organelle targeted for disruption. Bottom port 175 may serve to provide both the trapping electromagnetic radiation to a microfluidic chamber associated with a flow path 180 as well as to provide ablation electromagnetic radiation to the chamber.

In some embodiments an optomechanical system further includes a device for storing images detected by detector assembly. In other embodiments, a single device can perform both control and measurement functions (e.g., a device for storing images may be incorporated in an electronic controller).

An optomechanical system optionally includes microfluidic pathways for applications associated with moving single cells from a reservoir to platform 180. Such applications can employ any suitable type of microfluidic for a given application. Exemplary microfluidics can include, without limitation, microfluidic substrates, cells, tubes, ports and so forth and any combinations thereof. Such microfluidics can also comprise, for example, wells, channels, loading regions, loading ports, flow control channels, nutrient channels, mixing and reaction zones, recovery wells, arrays and combinations thereof. Exemplary microfluidics can also comprise silicon or other semiconductor materials such that a first emitter of a system of the invention can form an optomechanical trap through or substantially proximate to the microfluidic or a plurality of microfluidics, which can include, for example, wells, channels, loading regions, loading ports, flow control channels, nutrient channels, mixing and reaction zones, recovery wells, arrays and combinations thereof.

Referring again to FIG. 1, trapping laser line 110 and ablation laser line 115 traverse optomechanical system via reflective elements 145 and other conventional mirrors, amplifications, lenses, and so forth, as well as any combinations thereof, such as is shown in the figures by way of example only. These elements can be used with a system or method of the invention as well as any other suitable optical means, equipment components, devices and so forth as would be appreciated by one of ordinary skill within the art. In particular, it is understood that one or more trapping lasers from separate laser devices may be combined with one or more ablation lasers from separate laser devices to achieve an optomechanical system.

Labeling of target and non-target organelles can also permit additional optimization of organelle disruption using an optomechanical system or method provided herein. As described throughout the application, an optomechanical system can be used in automated configurations that minimize user intervention. Automation can be carried out by any suitable means such as, for example, computer control comprising control of a series of shutters, flipper mirrors, motorized stages, acousto-optic devices, analog-to-digital signal conversion (as well as combinations thereof) and incorporated in an optomechanical system to permit rapid data acquisition and position correlation.

Referring to FIG. 2, exemplary external electromagnetic radiation paths for trapping laser and ablation laser lines are provided. A device that emits electromagnetic radiation (EMR) includes any device capable of generating energy in the electromagnetic spectrum. Accordingly, the term "electromagnetic radiation" includes cosmic rays, gamma rays, x-rays, ultraviolet light, visible light, infrared light, radar, microwaves, TV, radio, cell phones and all electronic transmission systems. In this document, a device that emits electromagnetic radiation includes a "laser" device. Such devices are electromagnetic radiation emitting devices using light amplification by stimulated emission of radiation at wavelengths from 180 nanometers (nm) to 1 millimeter (mm). "Ablation lasers" and "trapping lasers" are examples of laser devices provided herein. As used herein, a "trapping laser" refers to a device that emits electromagnetic radiation suitable for trapping objects or particles by exploiting the properties of momentum associated with light. When light passes through a fluid medium, the optical path is bent by refraction in the fluid material. The bending of the light path corresponds to a transfer of momentum from the light to the refracting object or particle. The transfer of momentum exerts a force, which is capable of holding or manipulating the motion of the object or particle. This process is also designated "optical trapping." The term "laser ablation" refers to the process of using electromagnetic radiation to disrupt or modify a target object. An "ablation laser" refers to a device that emits electromagnetic radiation suitable for disrupting or modifying a target object.

Referring again to FIG. 2, the left panel shows the path of the ablation laser line. The laser line passes through a shutter, is optionally expanded, and directed onto a fast scanning mirror for beam steering. In this embodiment, the scanning mirror "steers" the laser across a target object while the target object remains substantially stationary. It is understood that the same or similar effect can be achieved by keeping the laser beam substantially stationary while moving a platform comprising a target object such that the object to be trapped or ablated can be moved in a pattern consistent with the targeted object. In this aspect, the object rather than the beam is moved such that the laser beam ablates the desired pattern consistent with the target object. In other aspects, controlled shields or masks can be used such that the desired target object can be ablated while other parts of, for example, a cell are shielded from ablation.

Referring again to FIG. 2, a beam may be directed to an open port associated with a microscope where a mirror reflects the beam up through the microscope stand and into the microscope objective. The right panel shows the radiation path of the trapping laser line and the externalized epi-fluorescence radiation path. The beam is optionally expanded by one or more biconvex lenses and mixed with the arc lamp emission with a short band-pass dichroic mirror. Custom dichroic mirrors in filter cubes housed in the microscope's reflector turret reflect the laser and part of the arc lamp's visible spectrum up into the microscope objective.

Figure 3:
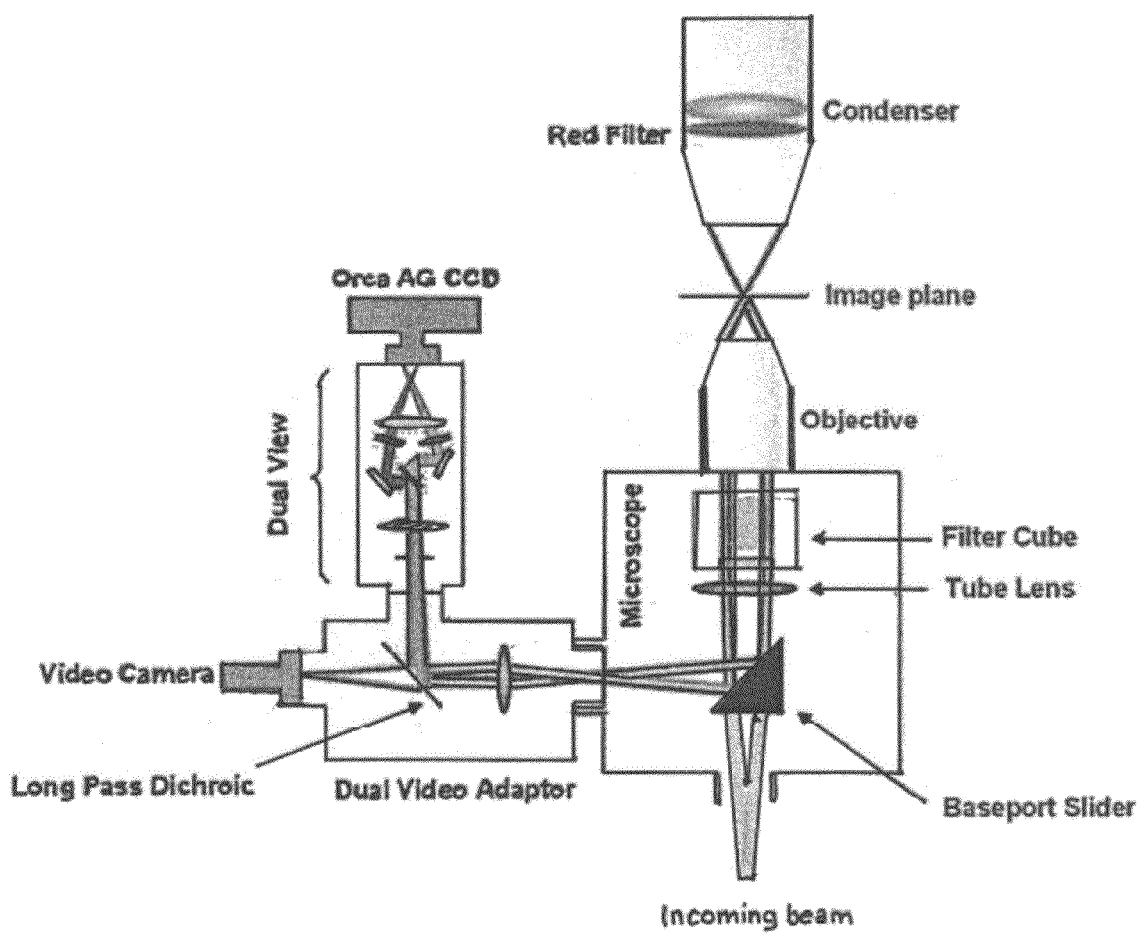
FIG. 3 depicts a flow diagram of various embodiments of a system.

FIG. 3 depicts exemplary internal radiation paths of a system provided herein. In this example, optics were chosen to passively mix and separate visible and near infra-red (NIR) radiation. Green laser light enters from underneath the microscope stand through a port (sometimes referred to as a "Keller" or "Keller-Berns" port) from below the microscope, the tube lens, one of the reflector turret's filter cubes, and the microscope objective. NIR radiation from a trapping laser and visible light from the arc lamp (both shown as circles in the filter cube) enter the back of the microscope stand, normal to the plane of the specimen in this figure, and are reflected upwards by one of the reflector turret's filter cubes. Long-red radiation from the halogen lamp may be selected by a filter in front of the condenser for phase contrast imaging. Optionally, visible emission from the specimen enters a dual video adaptor device modified to pass the long-red phase contrast light to the video camera and to reflect the shorter wavelength fluorescent emission up through the dual view system and onto the ORCA-AG CCD camera.

Figure 4:
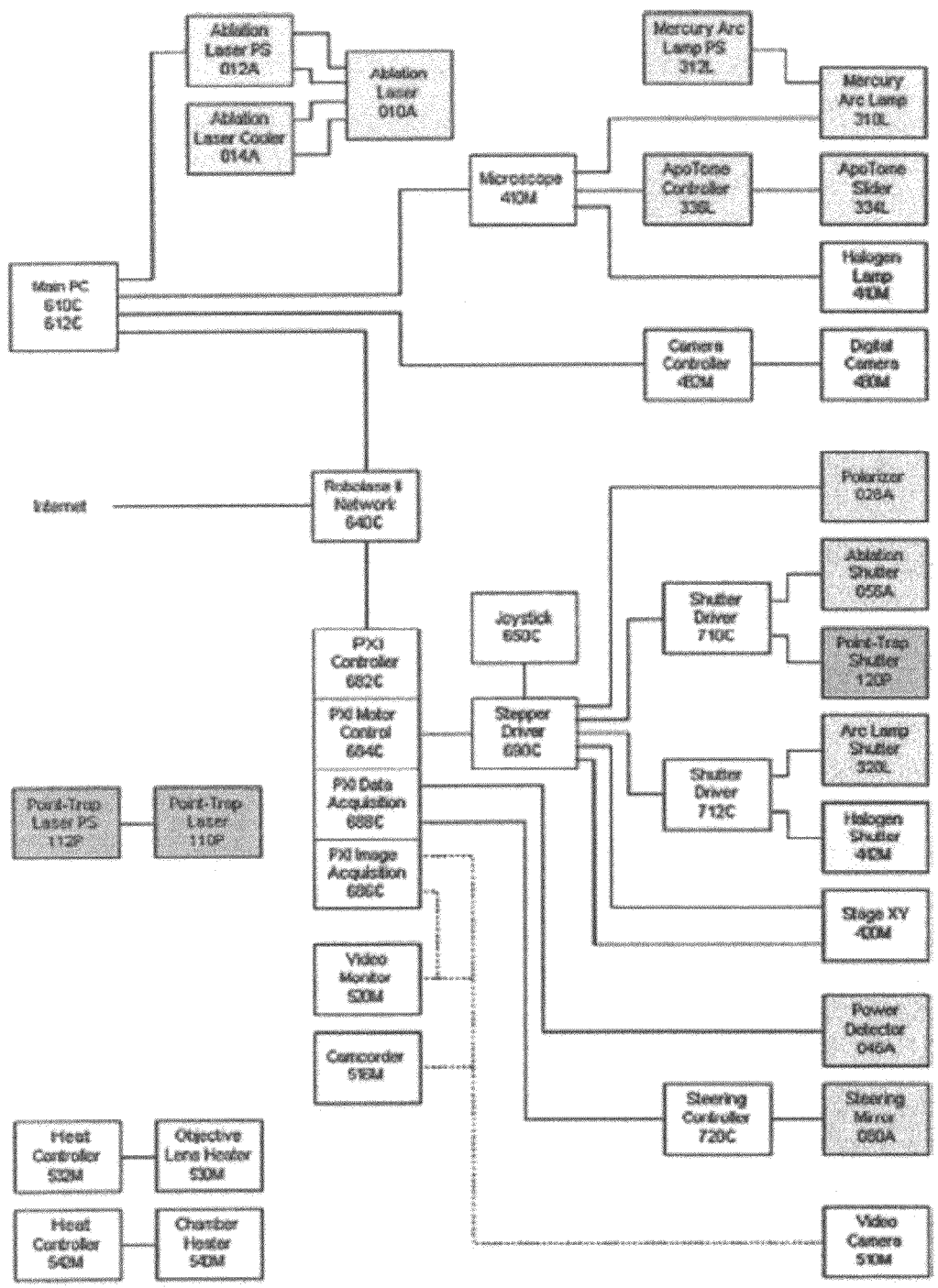
FIG. 4 depicts a control panel suitable for remote operation of a system.

Various exemplary embodiments of an optomechanical system are described in the flow diagram of FIG. 4. The flow diagram depicts connectivity between hardware associated with a system and software suitable for operating the system from a remote location.

Figure 5:
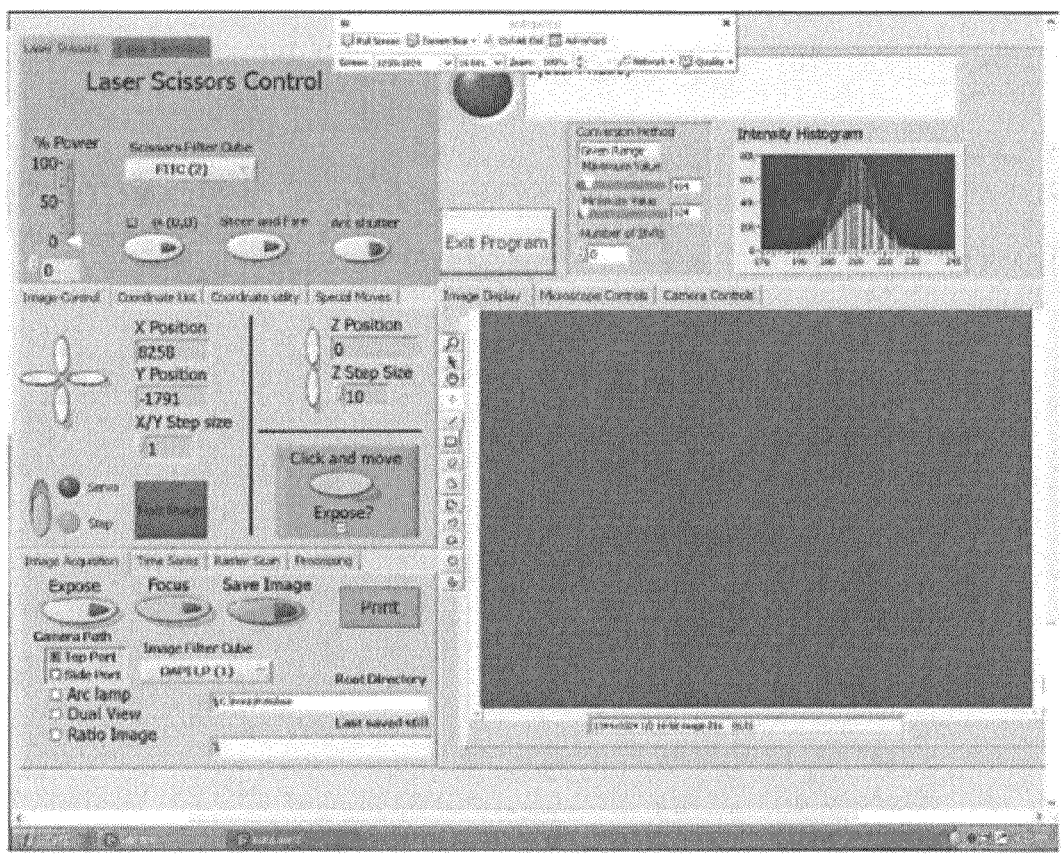
FIG. 5 depicts an exemplary remote session conducted via an Internet connection with a system.

FIG. 5 depicts exemplary control panel that may be used to monitor and control an optomechanical system. The gray box at the top of the screenshot is a drop-down menu to configure the session during operation of an optomechanical system. Shown are controls for stage movement, laser ablation, and image acquisition/display. The intensity histogram of each image may be displayed to aid in determining the proper setting for camera acquisition and image display.

Figure 6:
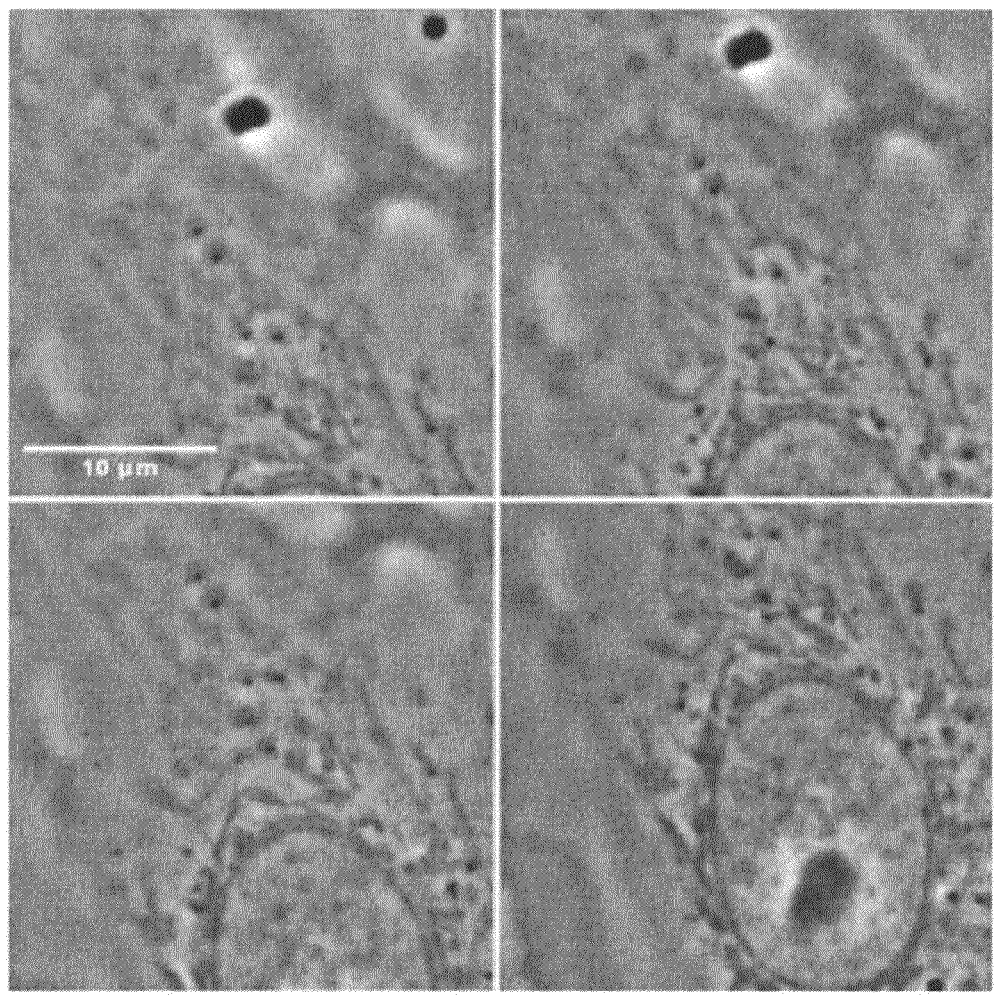
FIG. 6 depicts an exemplary remote session demonstrating remote fluorescence-guided subcellular surgery using a system.

FIG. 6 depicts an exemplary remote session in which PTK2 (rat kangaroo kidney) cells were imaged with a 63×PH3 1.4 na oil immersion objective. The user may remotely adjust the camera gain, acquisition time, and region of interest to optimize contrast and reduce image data size. Subfigure panels demonstrate remote operation of the X-Y stage and objective focus during a remote experiment. Note resolution of the nuclear envelope.

Figure 7:
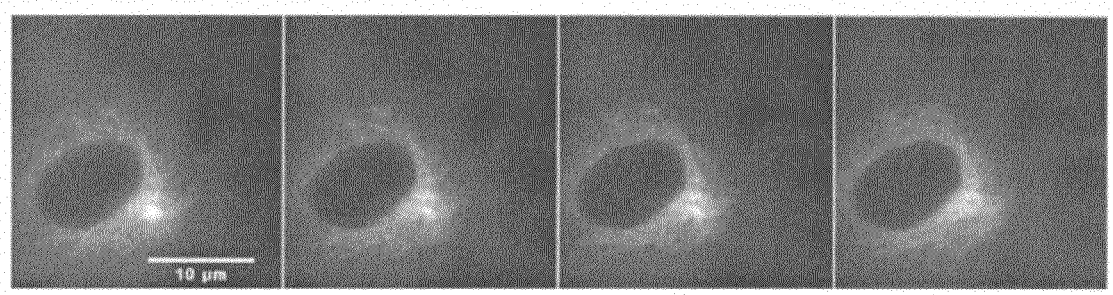
FIG. 7 depicts two exemplary remote sessions demonstrating remote laser ablation in phase contrast.

FIG. 7 depicts an exemplary remote session demonstrating remote fluorescence-guided subcellular surgery using an optomechanical system. The remote user searched for an appropriate cell and interactively focused and positioned the microtubule organizing center (a.k.a. centrosome) below the laser crosshair (first image). The next images show: post-firing of a 3 ms macropulse, the remaining region of the microtubule organizing center interactively positioned below the laser scissors crosshair, and a second 3 ms macropulse fired to delete the remaining microtubule organizing center.

Figure 8:
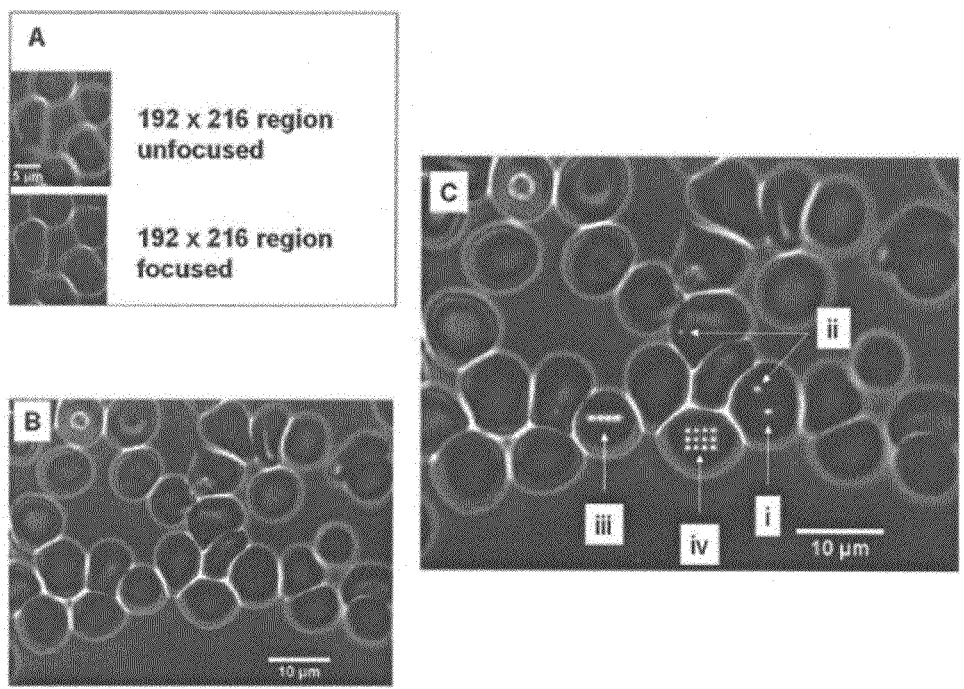
FIG. 8 depicts an exemplary remote session in which micron diameter microspheres were remotely captured using trapping lasers operatively associated with a system.

FIG. 8 depicts two exemplary remote sessions demonstrating remote laser ablation in phase contrast. Erythrocytes served as a convenient test specimen and targeting guide. Panel A shows an exemplary first session where a remote user has selected a region of interest of the CCD chip to speed image transfer for focusing the specimen. Shown is pre and post-focusing. Panel B shows a second exemplary session where a region of cells was brought into focus remotely. Panel C demonstrates optomechanical system beam steering capabilities by ablating at the center of the field (see crosshairs shown in FIG. 4) (see "i"), ablating single shots by beam steering (see "ii"), ablating along a line (see "iii"), and ablating within a remote user-defined rectangle (see "iv"). For examples iii and iv, the user defined the pixel radius of a single ablation, and the optomechanical system calculated the number of laser exposures necessary to fill the region in.

Figure 9:
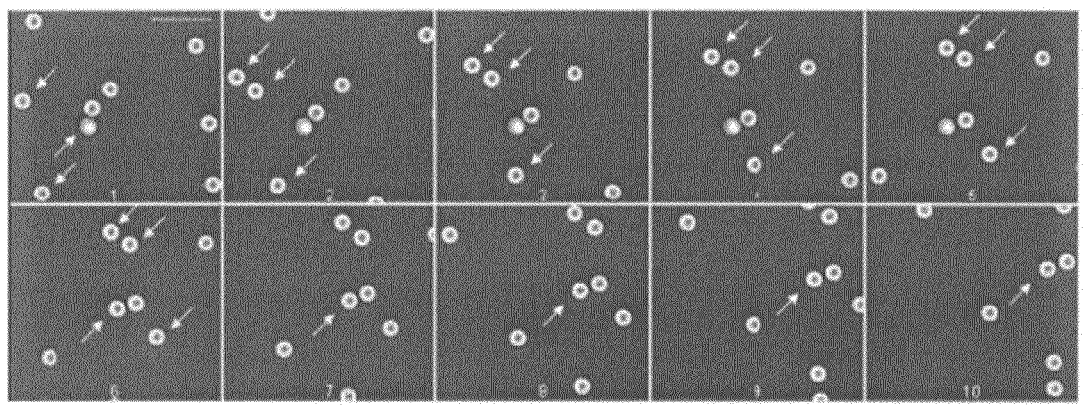
FIG. 9 depicts an embodiment of a system.

FIG. 9 depicts an exemplary remote session in which 10 micron diameter microspheres were remotely captured in the trapping laser line. The microspheres can be composed of any suitable material, such as polystyrene. Every fifth frame of an 8.2 frame/sec time series is shown. In frame 1, the two downward-left arrows (three arrows in subsequent frames) indicate reference microspheres moving through fluid flow in a 35-mm Petri dish. The upward-right arrow indicates a microsphere captured in the laser tweezers. A slight axial displacement of this microsphere (due to the laser tweezers) as compared with the free-floating microspheres can be observed, as the center dark region of the microsphere has transitioned to white. Frames 2-5 show the displacement of the reference microspheres relative to the trapped microsphere. Just prior to frames 6-10, the remote user released the microsphere from the trap through an optomechanical system control (note the reversal of the axial displacement), and the microsphere is carried away by the fluid flow. Note the second microsphere attracted to the laser focus but held away by the trapped one.

Figure 10:
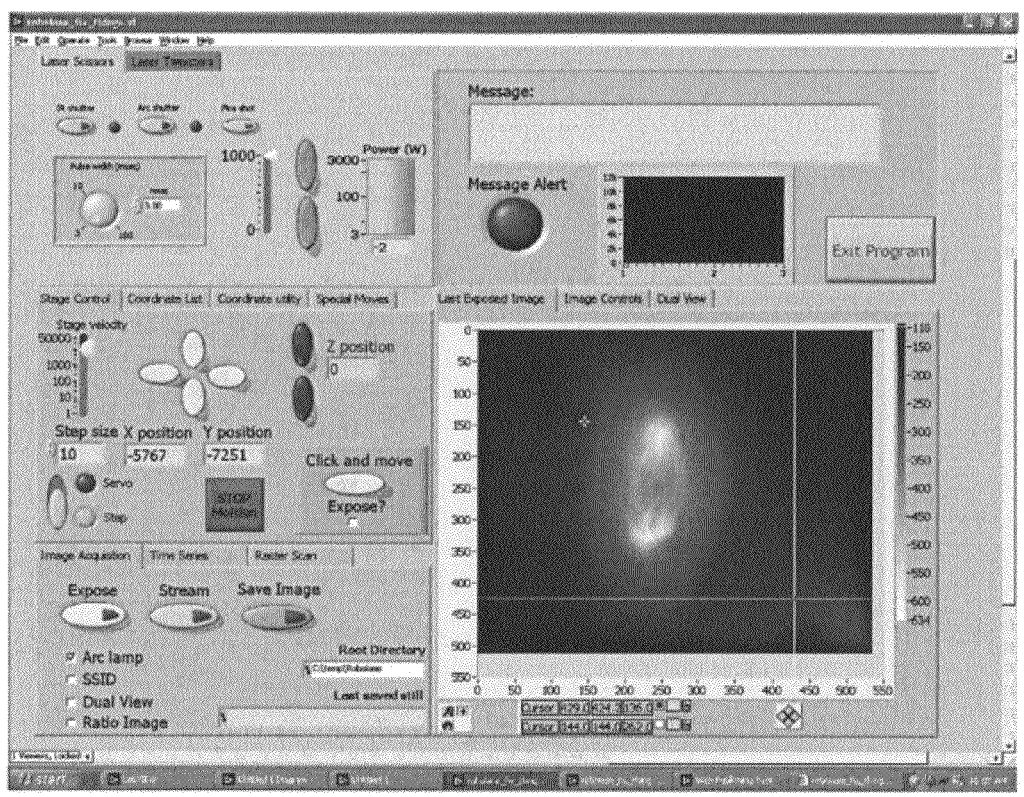
FIG. 10 depicts a graphical user interface suitable for interacting with a system.

FIG. 10 depicts an optomechanical system graphical user interface (GUI). The exemplary user interface of an optomechanical system is shown as it may be viewed on the host computer or from a remote site. The interface offers control of the microscope stage, laser power and exposure, arc lamp excitation, image acquisition and focus, or any combination thereof. The interface and its underlying functionality can be configured to automate a vast array of laser microbeam experiments, with appropriate user feedback and control.

Figure 11:
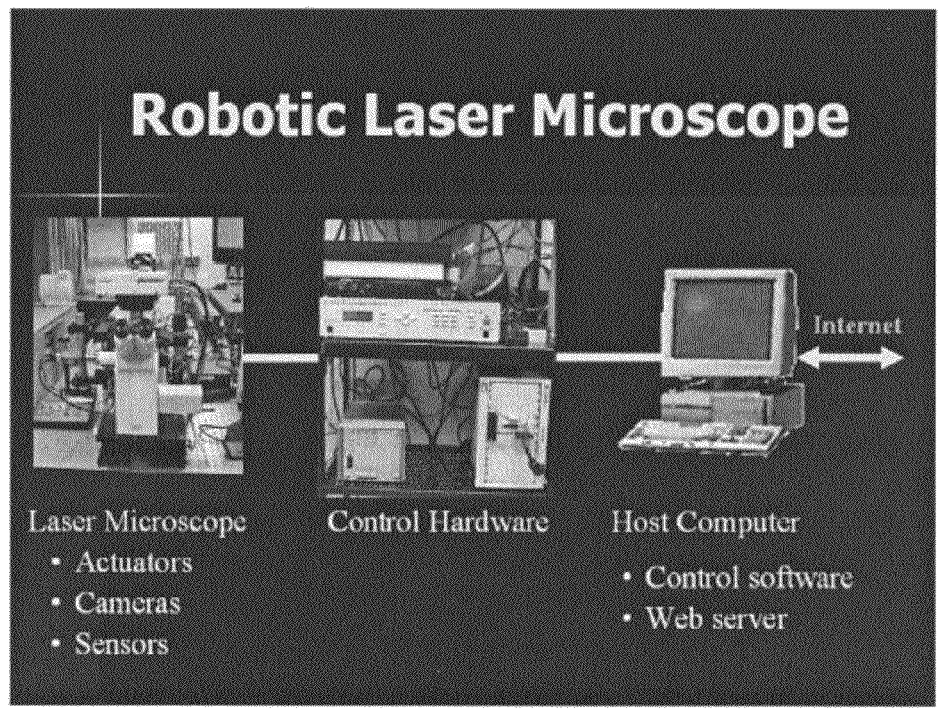
FIG. 11 depicts exemplary systems.
Figure 12:
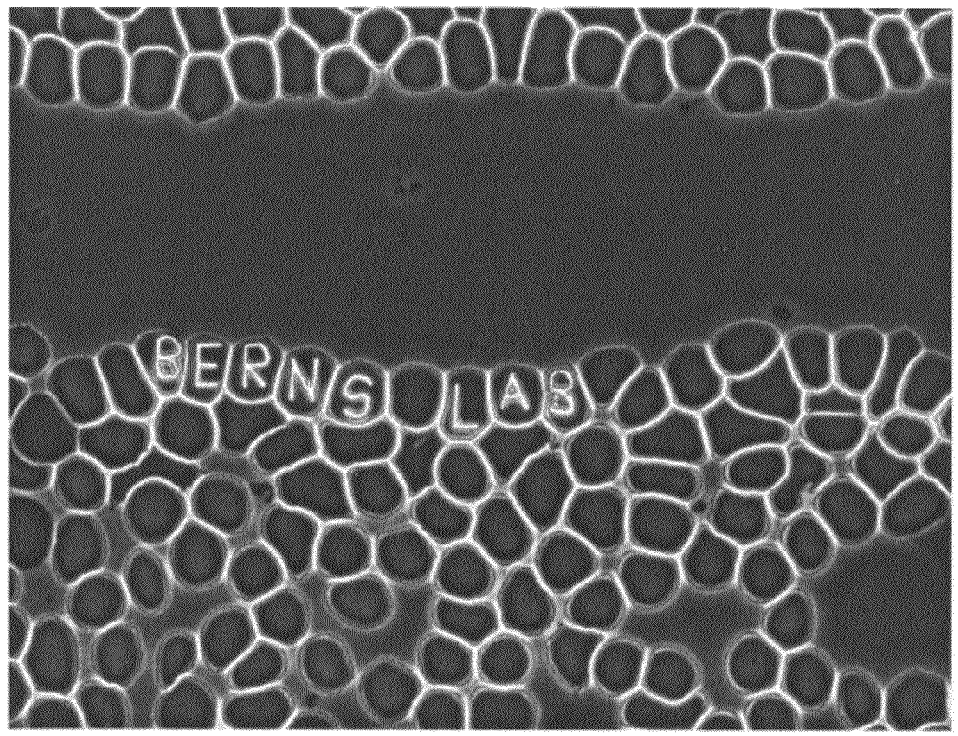
FIG. 12 depicts cells modified by a system.

FIG. 11 provides images of an embodiment of an optomechanical system. In this embodiment, three distinct elements are shown: 1) a laser microscope; 2) control hardware; and 3) a control software-web server. The exemplary optomechanical system includes hardware and software that allows the system to be controlled by remote users via the internet.

Figure 13:
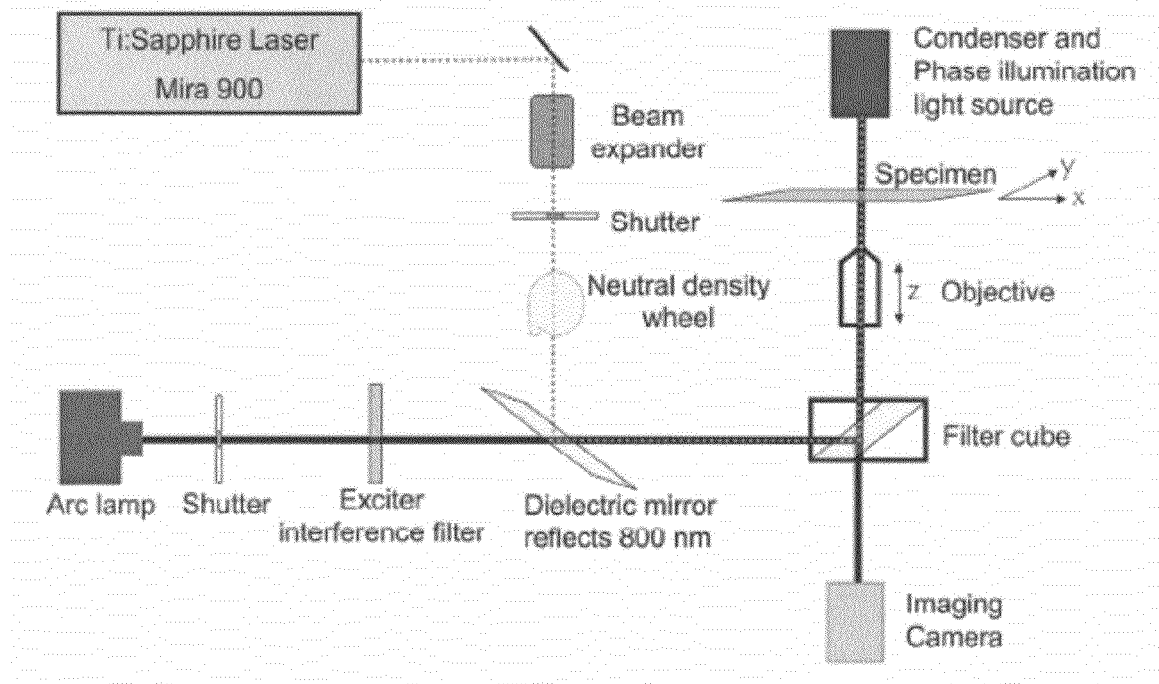
FIG. 13 depicts an embodiment of an optomechanical system that includes a Ti:sapphire laser emitting in the range of 100 to 300 femtosecond pulses at 72 MHz.

Referring to FIG. 13, a schematic diagram of an embodiment of an optomechanical system is provided. In this embodiment a Ti:sapphire laser beam is used to provide an ablation laser line. As shown in FIG. 13, the line may be expanded and passed through a shutter and neutral density wheel before being directed through the microscope and objective. The beam may be focused at the imaging plane. A dichroic mirror in the laser path reflects the beam and allows for fluorescence excitation light to transmit into the objective and illuminate the specimen.

The exemplary Ti:sapphire femtosecond laser is a Coherent Mira 900 Ti:sapphire laser (Coherent Incorporated, Santa Clara, Calif.) emitting at about 200 femtosecond pulses at about 76 MHz was used for ablation at 800 nm. Laser power was controlled manually by a neutral density wheel, which allowed regulation of beam power from 0 to 700 mW. Laser power was measured by a FieldMaxII TOP power meter coupled to a PM3 probe (Coherent Incorporated, Santa Clara, Calif.) with a 19-mm-diameter sensor. In this example the probe was placed directly after the objective where the diameter of the laser beam was smaller than the sensor diameter. This allowed for collection of all light exiting the objective, which resulted in an estimate of the power level at the focal point of the specimen. The diameter of the laser beam at the focal point was calculated from the equation $d=1.22\lambda/NA$, where $\lambda$ is the wavelength and NA is a numerical aperture of the objective. Laser exposure time was controlled by a motorized Oriel (Stratford, Conn.) electronic shutter controller, which allowed a minimum of 5-ms exposure time. Laser exposure times were set at about 150 ms. The beam was directed into the epi-illumination port of a Zeiss Axiovert 5100 2TV microscope (Carl Zeiss Incorporated, Thornwood, N.Y.) by a dichroic filter designed to pass visible arc lamp emission and reflect 800-nm laser light. The beam was focused by a Zeiss 63×PH3 oil immersion apochromat objective lens (numerical aperture 1.40).

Referring again to FIG. 13, targeting was accomplished by moving the stage (Ludl Incorporated, Hawthorne, N.Y.) by joystick control until the region of interest was positioned at the pre-aligned laser focal point. Laser ablation was accomplished by stage movement, such that the target region was exposed to the focused laser. Stage movement was controlled by a PCI-7344 motion controller and a MID-7604, 4 Axis Integrated Stepper Driver Power Unit (National Instruments), all controlled by software described in the present application. In this embodiment the optomechanical system included a 532-nm Spectra-Physics Vanguard laser with 76 MHz repetition rate and 80-ps pulse duration. Average power was attenuated by rotation of a neutral density wheel.

In this embodiment image acquisition occurred immediately before laser exposure, after laser exposure, and at preselected sequential time points following ablation. Twelve time series images were acquired at 5- to 7-s intervals. All controls for laser ablation and imaging may be located on a control panel described in the application A 75-W mercury/xenon arc lamp was used to excite fluorescence. Exposure of the sample to excitation illumination was controlled by a motorized Oriel mechanical shutter and varied from 0.5 to 2 s. An external excitation interference filter (CFP by 426 to 446 nm; YFP by 490 to 510 nm) was used to select the excitation wavelengths. The microscope filter cube included a beamsplitter and emission interference filter (CFP dichroic long-pass 455 nm/emission 460 to 500 nm; YFP dichroic long-pass 515 nm/emission 520 to 550 nm). Images were acquired using a Hamamatsu Orca C4742-95-12HR digital charge-coupled device (CCD) camera (Hamamatsu Corporation, Bridgewater, N.J.0. Images were stored as 16-bit tiff images.

In some embodiments an optomechanical system includes a fluorescence excitation source for YFP experiments. An exemplary excitation source includes an X-Cite 120 Fluorescence Illumination System (Exfo Photonics Solution, Incorporated, Ontario, Canada). Exposure of the excitation source was controlled by Zeiss Axiovert 200M. Images were acquired using a Hamamatsu Orca-ER C4742-80 digital CCD camera.

In another embodiment an optomechanical system may be used in methods related to nuclear inactivation of cells in a microfluidic flow path or cells growing on a flat surface. With regard to cells growing on a flat surface, the cells may be observed under a microscope using either alone or in combination under phase contrast, single or multiphoton fluorescence (or some other form of microscopy). This can be done in cells prior to fusion or after fusion. For example, the nuclei of a stem cell fused with a somatic cell may be identified by any number of methods: phase contrast microscopy, interference microscopy, morphology, fluorescence, location etc. Once identified, either by computer recognition or by a user, a laser of appropriate wavelength and energy parameters, will be focused on the nucleus or any other structure that is to be disrupted, eliminated, or inactivated. The laser may be scanned (i.e., translocated across the target object) to expose the entire nucleus, or the beam may be geometrically shaped to encompass the entire nucleus such that scanning becomes unnecessary, or the platform comprising a target object is translocated while the beam remains substantially focused and stationary, or any combination thereof. The result will be inactivation of the unwanted nucleus. Using a computer-controlled automated microscope, thousands of cell nuclei can be irradiated in several minutes, thus providing a high number of cells that contain the cytoplasm of the stem cell but only the programmed or to-be-reprogrammed nucleus of the somatic cell.

In another embodiment, inactivation of a target organelle in a cell is provided. The term "organelles" includes such cellular structures as the mitochondria, nucleus, endoplasmic reticulum, and microtubules of a target cell. In this embodiment, a target organelle associated with a cell in suspension or attached to a solid can be selectively disrupted or inactivated. For example, a stem cell nucleus can be inactivated as it passes through the focused laser beam in a flowing situation. The method is suitable for use in situations including: (a) inactivation of the stem cell nucleus prior to fusion, and (b) inactivation of the stem cells nucleus in the fused hybrid cell. With regard to example (a), the stem cell nucleus will be inactivated as it flows through the focused laser beam because of specific fluorescent molecules that are either being or have been expressed by the nucleus (thus making it detectable as well as sensitive to the laser light), or by some exogenous molecule that has been added to the cell suspension or microinjected, electroporated or introduced into the cell in any other way such that it is incorporated into the nucleus and makes the nucleus sensitive to the light. Thus, "photosensitization" of the target object using selective dyes is encompassed by the methods provided herein. The cell nucleus is inactivated as it passes through the laser beam. This may be accomplished in a microfluidic chamber or in a larger vessel more commonly used in FACS cell sorting machines. The cells with inactivated nuclei are then collected and used for the cell fusion process. With regard to example (b), the cells that are passed through the system are fused stem cells and somatic cells. The stem cell nuclei are destroyed/inactivated as they pass through the focused laser beam due to their having been pre-tagged with a dye or some other light-absorbing molecule (as described above) so that when these cells pass through the laser beam the light-absorbing molecule absorbs the light which in turn inactivates the nucleus of the stem cell. This can be performed in a microfluidic device or in a larger vessel used in standard FACS cell sorting machines.

A system provided herein may include a motorized inverted or upright microscope stand, external optics to direct the ablation and trapping lasers into the microscope, a CCD digital camera, a hardware-software suite for the control of laser power, the specimen stage, and microscope stand focus and illumination. The system is equipped with objectives of numerical aperture and working distance. In some embodiments, the system includes a fast scanning mirror that allows the laser beam that comes into the microscope to move in the microscope field by altering the position of the mirror. The control of the fast scanning mirror is accomplished by a computer which is interfaced with the computer keyboard's mouse and the scanning mirror hardware. The object can be outlined and excised (or exposed to the laser beam) by outlining it on the computer monitor (which projects an image of what is under the microscope). The outline is then converted into digital signals that then controls the movement of the scanning mirror. Thus the mirror moves in such a way that the laser beam follows the outline that the mouse made and destroys/dissects/exposes the specific target region that was outlined on the monitor screen using the mouse (or any other device such as a touch-screen pen).

In general, research microscopes have been developed to include motorized versions of their inverted microscopes. In exemplary embodiments, an optomechanical system utilizes a Zeiss Axiovert 200M with motorized objective turret, reflector turret (for fluorescence filter cubes), condenser turret, halogen lamp shuttering with intensity control, mercury arc lamp shuttering, camera port selection, objective focus, and parfocality adjustments for switching between objective lenses. The microscope also has a motorized optivar turret to increase the system magnification by 1.63 or 2.53. For laser ablation experiments, a 63× oil NA 1.4 plan-apochromat PH3 oil objective is used (though 100×, 40× and others can be used). The microscope stand has a built-in computer, which uses a controller area network (CAN) to communicate with motors and encoders within the microscope stand. The CAN receives commands through a serial interface typically attached to a computer running an image acquisition/microscope control program. Rather than using the software provided with the microscope, which was found to be cumbersome and slow for our purposes, custom control software capable of communicating with the CAN as described below was developed.

Features of the motorized microscope which are especially relevant to remote operation of a laser microscope are the shift-free reflector turret, microscope light path selection, illumination control, and objective focus. The shift-free reflector turret allows the user to repeatedly switch between any of five fluorescence filter cubes in the turret without a detectable pixel shift in the image. This is of great importance when performing resolution-limited targeting for laser ablation, as it ensures that the laser will always focus at the expected pixel location. Likewise, the Axiovert microscope can switch between camera ports repeatedly with no detectable pixel shifts when initiating an ablation sequence. One skilled in the art will recognize that other commercial microscopes provide similar or modified automated features that are compatible with this invention. In addition, such microscopes can be constructed to suit particular requirements under specific laboratory situations.

A Zeiss dual video adaptor is mounted on the left-hand camera port to allow simultaneous imaging of transmitted light and fluorescence. The 50/50 beam splitter shipped with the video adaptor was replaced with a long-pass dichroic mirror (640 DCLP Chroma Technologies, Rockingham, Vt.), which transmits longer red light and reflects the shorter visible spectrum upwards to the second camera. A band-pass filter centered at 680 nm (d680/603 Chroma Technologies) is placed in front of the condenser lens to limit the transmission light wavelengths. Fluorescence emission is reflected upwards by the dichroic mirror into a chromatic image splitter (Dual View, Optical Insights, Albuquerque, N. Mex.) that forms two images of the specimen simultaneously on the camera, representing two bands in the visible spectrum. The Dual-View image splitter also has a straight-through option mode with no image splitting. A closed circuit television camera may be mounted on the transmission port of the dual video adaptor for imaging bright-field or phase-contrast images from the long-red light path. Phase-contrast images can be captured with the high-sensitivity camera by removing the 680 nm band pass filter.

Referring again to FIG. 1, specimens may be mounted on platform 180 and platform may be associated with microfluidic devices suitable for presenting a cell to the platform. In one embodiment platform 180 is an X-Y stepper stage (Ludl Electronic Products Hawthorne, N.Y.) controlled with a National Instruments "flexmotion" PXI-7344 stepper motor controller and an MID-7604 power drive (National Instruments, Austin, Tex.). The flexmotion board may be mounted in a PXI electronic controller chassis for implementing software suitable for controlling system 100. Exemplary software includes the LabVIEW Realtime operating system, which is a graphics-free computing environment designed to maximize performance of control hardware. The optomechanical system host electronic controller communicates with the PXI chassis through a local area network (100 Mbps) running TCP/IP protocols. Optionally, an on-board program is included to run on the motion controller allowing local joystick control independent of both the host and the PXI electronic controller's CPUs. Motorized objective focus control may be achieved through the CAN by Zeiss' Harmonic Drive DC motor, providing 25 nm steps with 10 mm travel for precise focus control over multiple objectives' working distances. To achieve stable temperature control for specimens imaged by an oil-immersion objective lens, both the specimen and the objective lens may be heated. Specimens in 35-mm Petri dishes are heated with a stage heater (heater: DH-35; controller: TC-324B; Warner Instruments Corporation, Hamden, Conn.) while the objective is heated with a collar-type objective heater (heater: OBJSTD with controller, Bioptechs, Inc., Butler, Pa.). Other methods of temperature control are also compatible with embodiments of the optomechanical system.

The epi-illumination system was removed from the microscope stand for direct access by the trapping beam to the back aperture of the microscope objective. The epi-illumination system was mounted distal to the microscope and coupled through two 400 mm positive achromatic doublets (Newport Corp., Newport, Calif.) into the microscope. The motorized Axiovert is commercially supplied with a motorized shutter for the fluorescence light path which we removed because of inherent delays between computer commands to open the shutter and the opening event. Instead, an electronic shutter (Vincent Associates, Rochester, N.Y.) was mounted between the arc lamp and the epi-fluorescence lens system, with a notable decrease in delay time. Other methods of epi-illumination beam entry into the microscope are also possible, including normal entry through a fiber optic cable.

Connectivity of key controllers and actuators in an optomechanical system is demonstrated in FIG. 5. The unique identifiers in each block of the diagram (e.g., 610C) are for reference to an online reference manual available on the worldwide web at robolase.ucsd.edu. In the diagram the electronic controller is designated "Main PC." The electronic controller includes software suitable for operating an optomechanical system. Controller connects to the ablation laser and the microscope through two serial communications: to the ORCA camera controller through a firewire connection and to a PXI chassis through the optomechanical system local network. The PXI chassis contains a motion control card that connects to a stepper motor driver that responds to joystick commands, controls two shutter drivers, and drives the platform (e.g., XY microscope stage). The chassis optionally includes a data acquisition card that receives data from a power meter and communicates with the ablation laser's beam steering controller through analog voltage outputs. In this embodiment the optomechanical system can also operate with other chassis such as an MXI chassis.

Optics outside the microscope stand guide the ablation and trapping lasers into the microscope and supplies an optomechanical system with automated laser power control, laser shuttering, and laser power monitoring (see FIG. 1). An exemplary laser ablation radiation source includes a diode-pumped Spectra-Physics Vanguard with a second harmonic generator (SHG) providing TEM00 mode 532 nm laser light linearly polarized with 100:1 purity with a 76 MHz repetition rate, 12 ps pulse duration, and 2 W average power. The unattenuated laser power is far in excess of that necessary for resolution-limited subcellular laser ablation and left un-attenuated is well above the plasma threshold causing catastrophic damage to cells in the vicinity of the laser. The laser beam polarization purity is considerably increased from 100:1 through the first glan linear polarizer (CLPA-12.0-425-675, CVI Laser, LLC, Albuquerque, N. Mex.) with a $5 \times 10^5$ extinction ratio rotated for maximum transmission (95%). Laser power is controlled by rotating an identical glan linear polarizer placed in series to the first and mounted in a motorized rotational mount driven by an open loop 2-phase stepper motor with 0.05° accuracy (PR50PP, Newport Corp.). The stepper motor rotates the polarizer from its vertical orientation with maximum transmission (95%) to its horizontal orientation with minimum transmission well below the damage threshold of biological samples. The stepper motor is controlled via the flexmotion board in the PXI chassis. Light exiting the second polarizer is partially reflected by a laser-line beam sampler, with dual antireflection-coated surfaces. The sampled beam may be measured by a photodiode (2032 photoreceiver, NewFocus, San Jose, Calif.) and converted to a voltage. A calibrated photometer (1825-C, Newport Corp.) may be used to determine the relationship between the photodiode voltage and average laser power in the main beam. A mechanical shutter (Vincent Associates) with a 3-ms duty cycle gates the main laser beam to provide "short" bursts of pulses to the microscope.

The laser beam may be expanded using an adjustable beam expander (2-8×, 633/780/803 nm correction, Rodenstock, Germany) and lowered to a height just above the optical table by two additional mirrors. Telecentric beam steering is achieved by placing a single dual-axis fast scanning mirror (Newport Corp.) at an image plane conjugate to the back focal plane of the microscope objectives. This image plane is formed by a 250 mm biconvex lens positioned with its front focal plane at the image plane of the microscope Keller port (below the microscope stand) and with its back focal plane at the fast scanning mirror surface. To access the sub-microscope Keller port, the microscope is raised 70 mm above the table via custom-machined metal alloy posts to leave room for a 45° mirror, which vertically redirects incident laser light running parallel to the table through the Keller port (FIG. 3). Once inside the microscope stand, the laser light passes through the tube lens and one of the five fluorescence filter cubes of the reflector turret before entering the back of the objective lens. The reflector turret can be set up either with one filter slot blank or since the turret is automated, the system can position a fluorescence filter cube into place, with appropriate laser transmission characteristics. It is understood that the present invention encompasses microscope designs that do not bring the laser in through a Keller port.

All external mirrors in the ablation laser light path are virtually loss-less dielectric mirrors optimized for 45° reflections of 532 nm S-polarized light (Y2-1025-45-S, CVI Laser LLC, Albuquerque, N. Mex.).

In some embodiments the trapping laser light source is an ytterbium continuous wave fiber laser with a 5-mm collimator providing randomly polarized $TEM_{00}$ mode 1,064 nm laser output with 10 W maximum power (IPG Photonics Corp., Oxford, Mass.). Laser power is controlled programmatically through serial port communication. Laser light is reflected off two mirrors and into a custom beam expander comprised of two anti-reflection coated bi-convex lenses (f=100 mm, 400 mm) placed telescopically to expand and collimate the beam. The 100 mm lens is placed so that its back focal plane lies on the surface of the second mirror, which is mounted in a second dual-axis fast scanning mirror (Newport Corp.) to achieve telecentric beam steering in the specimen plane. The laser then reflects off a 2 inch diameter short pass dichroic beam splitter placed behind the microscope in the arc lamp illumination light path to merge the two light paths. Laser light is then reflected upwards by a dichroic mirror mounted in the reflector turret, and into the back of the objective lens where it is focused in the specimen plane. The 100 mm lens mount can be adjusted axially to move the laser trap depth relative to the image plane. A mechanical shutter is placed in the beam path and is controlled by the flexmotion controller. All external mirrors in the trapping laser light path are virtually loss-less dielectric mirrors optimized for 45° reflections of 1064 nm S-polarized light (Y1-1025-45-S, CVI Laser).

A detector assembly may include a high quantum efficiency digital camera to capture transmitted and fluorescent images. In some embodiments, an optomechanical system implements a Hamamatsu Orca-AG deep-cooled 1,344×1, 024 pixel 12-bit digital CCD camera with digital (fire wire) output. The ORCA can read out sub regions of the chip for increased frame rates, bin pixels for increased signal-to-noise, and adjust gain and exposure time to trade off between signal-to-noise characteristics and arc lamp exposure times. An optomechanical system may use Hamamatsu's Video Capture Library for LabVIEW (ver 1.0) plug-in to communicate with the ORCA camera controller through its DCA-MAPI driver (FIG. 4).

Various software may be engaged during operation of an optomechanical system. In one example, a hardware control suite and web server software are used for sharing an optomechanical system with remote users. Exemplary control software programmed in the LabVIEW 7.1 (National Instruments) programming language may be used to control the microscope, cameras, and external light paths associated with an optomechanical system. The control software also manages image and measurement file storage. It communicates with the user through the graphical user interface or the control panel in LabVIEW. The control panel receives user input and displays images and measurements. The control software interprets commands sent by the user into appropriate hardware calls and returns the results of that action to the front panel and/or computer's hard drive.

As noted above, FIG. 5 provides a snapshot of the front panel. The upper-left panel contains laser parameter controls. This panel contains two tabs: one in green to control the ablation laser and one in blue to control the trapping laser. Ablation laser controls include a slider to select power in the focal plane, two buttons to fire the laser either at the center of the field or at the green crosshairs which are positioned with the mouse, and selection of the filter cube turret position during ablation. Once either fire button is pressed, the control software calls the microscope CAN to select the Keller port and the appropriate filter cube. The control software then continuously quarries the CAN to ensure the completion of both actions before opening the shutter for a single 3 ms laser burst. Beam steering is sufficiently faster than the camera port and filter turrets, such that a quarry of its position prior to opening the shutter is unnecessary. Laser tweezers controls (not shown) include laser power selection, shutter state and beam positioning controls.

Referring to FIG. 5, the center panel on the left contains stage and ablation laser steering controls. The "stage control" tab contains left/right and up/down rockers to move the microscope stage with position feedback. A slider selects either step or servo mode to move the stage either in increments specified in the "X/Y Step Size" control, or continuously while the rockers are pressed. A similar pair of rockers moves the microscope objective for focus control. The "Click and Move" control is a novel control designed to minimize exposure of the cells to the arc lamp light during stage movements. The user simply chooses the crosshair tool from the toolbar to the left of the image and clicks on an object of interest in the image. The program then calculates that pixel's displacement from the field of view center and moves the stage to center the object. The "Expose?" check box provides the option to follow the move with an exposure. The "Coordinate List" tab allows the user to store the current position in a list or to return to any stored coordinate. The "Coordinate Utility" tab allows the user to load an old list of coordinates, to clear the current list, or to save the current list to the hard drive. The "Special Moves" tab contains controls for beam steering and for laser ablation through a series of z-coordinates. The user can select the rectangle tool from the tool bar and draw a rectangle around a region in the image. There is a control in this tab to carve out that rectangle by firing single macropulses (one opening of the mechanical shutter which will pass multiple individual laser pulses) at evenly spaced locations in the rectangle. Since the laser causes nearly diffraction-limited ablation, the program calculates the number of macropulses necessary to fill in the rectangle-based on the pixel dimensions of the rectangle and the pixel extent of a single diffraction-limited ablation. It is understood that the control panels described above and elsewhere in this document are exemplary only. The skilled artisan will recognize that a system provided herein can be controlled by any type of panel suitable for monitoring and managing the activities of the system. Such panels can be modified to accommodate additional functions according to a users specific requirements.

Referring again to FIG. 5, the lower panel on the left contains image acquisition controls. The "Image Acquisition" tab contains controls for exposing single images, continuous acquisition (Focus), image storage, and image printing. The user can select the filter cube to place during the acquisition, whether to gate the arc lamp during the exposure, and controls to calculate a ratio image when used with the chromatic image. The "Root Directory" control specifies the top directory for file saving using our automated file naming system, and an indicator displaying the full path and name of the last saved image. The file path and name are designed to prevent accidental overwriting of data during successive operations of the program, coding the file name with the current time. The "Time Series" tab contains controls for acquiring a time series of images. The time series uses setting from the "Image Acquisition" tab and contains controls for the number of images and the duration between images as well as an indicator of the last image saved in the time series. The "Raster Scan" tab has a control to raster through user-selected stage coordinates and acquire images at those locations at time durations set through a control.

Referring to FIG. 5, the lower panel on the right contains camera and microscope controls. The "Image Display" tab displays the last acquired image plus the toolbar for selecting ablation and click-and-move coordinates. The "Microscope Control" tab contains controls for the microscope stand to select the objective, filter cube, condenser filter, optovar, and image port. The "Camera Controls" tab contains controls for camera gain, digitization offset, exposure time, and binning. It also contains an area-of-interest control to only transfer image data from an area of interest defined with the rectangle tool in the image display. Lastly, this tab has controls for click and move parameters including pixel coordinates of the field of view center and the pixel/microscope step gain.

The upper panel on the right contains a message box and the image histogram. The message box displays important messages, such as error notifications or equipment status, and draws user attention by pulsing the large green digital LED to the left of the message box when a new message arrives. The gray box controls the image display lookup table for mapping 12-bit images to the 8-bit display. This control uses four modes of look-up table: (1) Full-dynamic, in which the range of nonzero intensities are divided into 256 equally spaced bins, (2) 90%-dynamic, in which the dynamic range containing the middle 90% of the cumulated histogram of the image is divided into 256 equally spaced bins, (3) Given-range, in which the range of grayscale values specified by the "Maximum Value" and "Minimum Value" slider controls are equally divided into 256 bins, and (4) Down-shift, in which the grayscale values are shifted to the right in 8-bit increments, as specified by a control. An image histogram displays the pixel intensity histogram of the last acquired image to aid in the selection of an appropriate lookup table and to quantify separation between the background noise mode and the pixels of interest.

Two web server packages were compared. The first is the "remote panel" feature provided by National Instruments as a feature of LabVIEW. The LabVIEW web server publishes the control panel as an html document to which multiple users can log on during runtime. Once users connect to the an optomechanical system webpage, the front panel of An optomechanical system will appear in their web browser window with all the functionality available to a user operating from the host computer. Those logged on can either participate as an observer, or request control of the control panel to perform an experiment. It is not necessary for the remote user to have LabVIEW installed. To operate the An optomechanical system remote panel, it is only necessary to install the free LabVIEW run-time engine installed automatically at the first connection to any remote panel. The server can be configured to allow browser access for viewing, viewing and controlling, or to deny access to a programmable list of IP address. The LabVIEW protocol works by only transmitting changes to the control panel as they occur, as opposed to continuously transmitting the entire control panel as well as the states of the buttons and controls.

The second web server is a web-based protocol "Log me in" available on the world wide web at "logmein.com" (3 am Labs, Inc., Woburn, Mass.). This exemplary protocol belongs to a family of software that allows remote control of a PC through a live window that functionally duplicates the host PC from anywhere with an Internet connection. The protocol uses a peer-to-peer session handoff to provide high-speed remote control by eliminating the gateway, thereby allowing the two PCs to communicate directly. The logmein.com host computer maintains a constant secure sockets layer (SSL)-secured connection with one of the logmein.com gateways. This link is initiated by an optomechanical system and the firewall treats it as an outgoing connection. The client browser operated by a remote user establishes a connection to Logmein.com and authenticates itself after which the gateway forwards the subsequent encrypted traffic between the client and the host. The remote user is not required to download additional programs to connect to an optomechanical system; however, there is an optional ActiveX control download to improve image quality. The user can switch the host's display between "low quality" 8-bit color images and "high quality" 16-bit color images during the session to trade off between color resolution and frame transfer rates.

It is known that reprogramming of a stem cell is possible by fusion of a somatic cell nuclei with human embryonic stem cells (Science, 309:1369-1372, 2005). By placing somatic cell nuclei (specifically from skin fibroblasts) into the cytoplasm of stem cells via standard cell fusion methods, it has been possible to activate genes that had long been silent in the somatic cell nuclei taken from the adult donor. These may be genes that cause the descendants of the fused cell to differentiate into any number of cell/tissue types. It has been suggested that the cytoplasm of the stem cell contains biochemical factors/signals that cause the somatic cell chromosomes/genes to be activated and/or re-programmed thus resulting in a cascade of biochemical signaling ultimately resulting in the production of molecules and structure of virtually any tissue type. How the above steps will be understood and eventually harnessed to produce new tissues and organs, and to help in the understanding of disease processes that affect these tissues, will be a major area of research and development for many decades to come.

In somatic cell nuclear transfer, or any other mode of generating stem cells that involves placing a somatic or other (zygote, embryo, fetus, transplant or implant) nucleus into an ovum, early embryo, fetus or other cell type at any other stage of embryonic or post-natal stage of development, it may be desirable to remove, destruct or biologically inactivate the DNA or RNA genomes of the host cell, i.e. the fused or pre-fused cell, whether these genomes be nuclear, mitochondrial, chloroplast, viral, viroid or any other endosymbiotic or infectious agent with a genome composed of DNA, RNA or both.

As early as 1969, Berns used a microscope-focused laser beam to excise small regions of chromosomes in living cells (Berns et al., Nature 221: 74-75, 1969; Berns et al., Exp. Cell Res. 56: 292-298, 1969; Berns et al., J. Cell Biol. 43: 621-626, 1969). This was followed by the demonstration that the laser beam could be used to inactivate genes (reviewed in Berns and Rounds, Sci. Am. 222: 98-103, 1970) and more recently, that genes could be inactivated on chromosomes by using multiphoton absorption (Berns et al., PNAS 97: 9504-9507, 2000). The contents of these publications are incorporated herein by reference in their entirety.

Provided herein are systems and methods for high throughput imaging and modification of a target cellular organelle in a cell, such as a stem cell nucleus. The cell may be growing flat in a dish, or unattached in suspension. A system may be engineered to include a robotic laser ablation and tweezers microscope. The system may be configured to be operated via the internet using most Internet accessible devices, including laptops, desktop computers, and personal data assistants (PDAs). The system affords individual users the ability to conduct micromanipulation experiments (cell surgery or trapping) from remote locations. A system described herein greatly expands the availability of complex and expensive research technologies via investigator-networking over the internet, or via direct high speed optical connections between institutions.

The system offers three unique features: (1) the freedom to operate the system from any internet-capable computer, (2) the ability to image, ablate, and/or trap cells and their organelles by "remote-control," and (3) the security and convenience of controlling the system in the laboratory on the user's own personal computer and not on the host machine.

Time delays between commands received on the host computer and the completion of actuation were characterized by programmatically placing timers in the system control software. Time delays during switching between ablation and imaging were maximized during measurement by imaging through the binocular port with filter cube 2 and ablating from the Keller port through filter cube 5. When switching from imaging to ablation, the system takes 610, 19, and 20 ms (mean, standard deviation, and N) for the imaging port transition and 688, 6, and 10 ms for the filter cube transition, with a total duration of 1400, 41, and 10 ms from the press of the button to the completion of the ablation, with a 3 ms laser exposure time. A t-test showed no significant increase in total ablation time when the laser is steered before the ablation ($P>0.05$, $N=10$ for both samples). The imaging port transition required switching both the base port slider and the side port turret. When switching from ablation to imaging, the system takes a total 1387, 103, and 10 ms to transition the imaging port and the filter wheel followed by 677, 34, and 10 ms or 702, 34, and 10 ms for the subsequent image with or without operating the arc lamp shutter, respectively. The images were acquired in snap mode with a 1 ms exposure time to measure the latency of the camera digitization and readout. Computational latency during continuous image acquisition was quantified by measuring the total time to acquire a set of images (1 ms exposure time each) in which the size of the sets ranged from 23 to 36 individual images. The total times of ten sets were recorded and averaged within the sets with a between-set average 133, 3, and 10 ms per image delay time.

In one example, a connection between San Diego, Calif., USA and Boca Raton, Fla., USA using a hotel administered T1 connection operating at a maximum of 10 Mbps was established. This experiment tested remote control of the microscope stage movement and control of objective focus (see FIG. 6). High resolution images were acquired with a 63×PH3 phase contrast NA1.4 oil immersion objective. This experiment implemented the LabVIEW web server for remote operation. Note the resolution of the double-membrane nuclear envelope. Images transfer times were 2-3 s per image for a 256×256 sub-region of the CCD.

A second experiment was conducted from Boca Raton, Fla. (USA), again implementing the LabVIEW web server. In this experiment, cells with green fluorescent protein labeled microtubules were observed and manipulated under phase contrast and epi-fluorescence illumination (FIG. 7). In these cells, the centrosome microtubule organizing center (MTOC) was irradiated with the laser scissors. The MTOC region was irradiated at three different time points, with a progressive loss of fluorescence with each laser exposure. In this experiment, the following remote procedures occurred: (1) the microscope stage was moved until an appropriate cell was located, (2) the microscope was focused at different z-axis optical planes in the cells to determine the desired optical plane for laser exposure, (3) laser parameters (wavelength, power/energy, and number of exposures) were selected, (4) the laser was targeted to a specific region (the MOTC) in the cell, and (5) the result was digitally recorded and the cell was followed for a desired time period. In this particular cell, two laser exposures were performed until the desired ablation was observed.

a third experiment, which was conducted from Brisbane, Queensland, Australia implemented the Logmein.com web server. In this experiment beam steering for remote laser targeting and ablation over a long-distance internet connection was demonstrated (FIG. 8). Nucleated red blood cells were deposited on a microscope cover glass by the smear method and mounted in a Rose chamber in San Diego Calif. Remote control of the system from Australia successfully demonstrated (1) all of the manipulation capabilities described in the previous experiment, (2) that the ablation laser beam could be moved to different locations in the same cell, with a spatial resolution of less than a micron for both the lesion diameter as well as the distance between individual lesions, and (3) that multiple discrete visible lesions could be placed in the same cell. The time from initial remote command (pressing of the fire button) in Australia to actual observation of the event on the host system was determined by measuring delay times between oral communication of the command over a telephone connection and actuation of the command on system. Any delay time was unperceivable. Full-frame transfer rates were measured by counting the number of screen refreshes per 10 s interval. An 8.2 frames/s rate measured from the system host computer corresponded to 1.5 frames/s in low quality mode and 0.7 frames/s in high quality mode.

A fourth experiment, conducted from Atlanta, Ga., implemented the Logmein.com web server. In this experiment, 10 μm diameter fluorospheres (Coulter Corp., Hialeah, Fla.) were suspended in water in a 35 mm glass-bottom Petri dish in which thermal flow in the water was induced by heating the objective lens using the objective heater set at 37° C. The remote user selected "focus" mode on the control panel to stream images across the internet. The remote user was able to open and close a mechanical shutter, allowing the trapping beam to be focused on the target microsphere through a push-button control in the laser tweezers tab of the control panel. A time series was recorded after a microsphere was trapped and then released to demonstrate the ability of a remote user to manipulate objects with the laser tweezers (FIG. 9). A 40× oil 1.3NA PH3 objective lens was used.

Provided herein are various optomechanical systems that can be operated via the Internet using most internet accessible devices including laptops, desktop computers, etc. These systems afford investigators the ability to conduct micromanipulation experiments (cell surgery or trapping) from remote locations. These systems greatly expand the availability of complex and expensive research technologies via investigators networking over the internet or other high speed dedicated communication lines. It serves as a model for other "internet-friendly" technologies leading to large-scale networking and data-sharing between investigators, groups, and institutions on a global scale. In various embodiments, an optomechanical system provides: (1) the freedom to operate the system from any internet capable computer, (2) the ability to image, ablate, and/or trap cells and their organelles by "remote-control," and (3) the security of operating the system in house from the researcher's own laptop without the risk of leaving data on the host computer. Provided herein are examples of: (1) precise control of microscope movement and live cell visualization, (2) subcellular microsurgery on the microtubule organizing center of live cells viewed under phase contrast and fluorescence microscopy, (3) precise targeting of multiple sites within single red blood cells, and (4) laser trapping of an individual cell.

An optomechanical system provided herein is applicable in a wide array of live cell experiments and commercial applications relative to medicine. The exemplary ablation laser wavelength of 532 nm lies within the excitation band of many common fluorophores, including GFP, YFP, and FITC so that in some embodiments ablation would only require changing the imaging path and not the reflector position. In this case, image acquisition could begin about one and one-half seconds after initiation by the user. Researchers studying changes immediately following the ablation (in the first 4 s), for example cytoskeletal dynamics, could interface the ablation laser into the epi-fluorescent light path.

The examples set forth above are provided to give those of ordinary skill in the art a complete disclosure and description of how to make and use the embodiments of the apparatus, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
   (a) directing a target object comprising an organelle to a platform that receives an ablation radiation
   (b) photosensitizing the organelle to the ablation radiation;
   (c) generating an image of the target object on the platform;
   (d) generating an outline of the photosensitized organelle based upon the image; and
   (e) emitting the ablation radiation toward the specimen to selectively disrupt the photosensitized organelle wherein the emitting comprises at least one of:
      (i) emitting the ablation radiation based on a shape determined by the organelle outline;
      (ii) translocating the ablation radiation in a movement pattern determined by the organelle outline; and
      (iii) maintaining the ablation radiation substantially stationary while translocating the target object in a movement pattern determined by the organelle outline.

2. The method of claim 1, wherein directing the target object further comprises flowing the target object through a flow path.

3. The method of claim 2, wherein flowing the target object through the flow path occurs while emitting the ablation radiation toward the target object.

4. The method of claim 1, wherein the ablation radiation is emitted by a laser.

5. The method of claim 4, wherein the laser is a gas laser, a solid-state laser, a tunable dye laser, or semiconductor laser.

6. The method of claim 5, wherein translocating the ablation radiation comprises scanning by a scanning mirror.

7. The method of claim 1, wherein the organelle is a nucleus.

8. The method of claim 7, wherein the target object comprises a stem cell fused to a somatic cell, the stem cell comprising cytoplasm and the nucleus, and the somatic cell comprising a programmed nucleus.

9. The method of claim 8, wherein emitting the ablation radiation toward the target object to selectively disrupt the sensitized organelle comprises:
   inactivating the nucleus of the stem cell such that the stem cell fused to the somatic cell forms a fused cell comprising the cytoplasm of the stem cell and the programmed nucleus of the somatic cell.

10. The method of claim 9, wherein inactivating the nucleus of the stem cell comprises at least one of inactivating, removing, and destroying a nucleic acid of the nucleus.

11. The method of claim 1, wherein photosensitizing the organelle comprises tagging the organelle with a light-absorbing molecule.

12. The method of claim 11, further comprising exciting fluorescence of the light-absorbing molecule while emitting the ablation radiation, wherein the light-absorbing, molecule is a fluorescent molecule excitable by the ablation radiation.

13. The method of claim 1, further comprising, before emitting the ablation radiation, shielding a portion of the target object from being disrupted.

14. The method of claim 1, further comprising fusing a stem cell with a somatic cell to form the target object, the target object being a fused cell.

15. The method of claim 1, wherein the platform further receives a trapping radiation.

16. The method of claim 15, wherein emitting the ablation radiation toward the target object comprises emitting the ablation radiation sufficient to disrupt the organelle while emitting the trapping radiation sufficient to trap a cell containing said organelle.

17. The method of claim 15, further comprising photosensitizing the organelle to the trapping radiation.

18. The method of claim 15, wherein the trapping radiation has a wavelength between 750 nm and 1250 nm, and the ablation radiation has a wavelength between 375 nm and 625 nm.

19. A method comprising:
   (a) directing the target object to a platform that receives a first radiation configured to selectively trap the organelle and an ablation second radiation configured to selectively disrupt the organelle;
   (b) photosensitizing the organelle to the ablation radiation;
   (c) generating an image of the target object on the platform;
   (d) generating an outline of the photosensitized organelle in the image;
   (e) generating signals corresponding to the organelle by digitizing the organelle outline;
   (f) transmitting the signals to an electronic controller operatively associated with an emitter; and
   (g) emitting the ablation radiation toward the target object to selectively disrupt the photosensitized organelle.

20. The method of claim 19, wherein emitting the ablation radiation comprises at least one of:
   (i) emitting the ablation radiation in a geometric shape determined by the signals;

(ii) translocating the ablation radiation in a movement pattern determined by the signals; and
(iii) maintaining the ablation radiation substantially stationary while translocating the target object in a movement pattern determined by the signals.

* * * * *